United States Patent [19]

Schreurs et al.

[11] Patent Number: 5,449,765
[45] Date of Patent: Sep. 12, 1995

[54] DNA ENCODING AMINO ACIDS 590–710 OF GLYCOPROTEIN GII OF PSEUDORABIES VIRUS

[75] Inventors: Christa S. Schreurs, Kerken; Thomas C. Mettenleiter, Tübingen; Artur J. Simon, Munich; Noëmi Lukacs, Düsseldorf; Hanns J. Rziha, Tübingen, all of Germany

[73] Assignee: Akzo N.V., Arnhem, Netherlands

[21] Appl. No.: 332,610

[22] Filed: Oct. 31, 1994

Related U.S. Application Data

[60] Continuation of Ser. No. 207,905, Mar. 7, 1994, abandoned, which is a continuation of Ser. No. 740,739, Aug. 6, 1991, abandoned, which is a division of Ser. No. 383,833, Jul. 21, 1989, Pat. No. 5,196,516.

[30] Foreign Application Priority Data

Aug. 1, 1988 [EP] European Pat. Off. .......... 8812479

[51] Int. Cl.$^6$ ...................... C12N 15/33; C12N 15/03; C12N 15/04
[52] U.S. Cl. ................... 536/23.4; 536/23.72; 435/172.3; 435/252.3; 435/69.3; 435/69.7; 424/186.1; 424/229.1
[58] Field of Search ............... 536/23.72, 23.4; 435/69.3, 69.7, 252.3, 172.3

[56] References Cited

FOREIGN PATENT DOCUMENTS 0162738 11/1985 European Pat. Off. .
0261940 3/1988 European Pat. Off. .

OTHER PUBLICATIONS

T. C. Mettenleiter et al., Chemical Abstracts, vol. 105, No. 4, Jul. 28, 1986, p. 168, col. 1, Abstract No. 36564n.
Robbins et al. 1987 J. Virology 61(9): 2691–2701.
Watsen, James D. 1987, Molecular Biology of the Gene, The Benjamin Kummings Publishing Company, Inc., Menlo Park, Calif. p. 313.

Primary Examiner—Keith C. Furman
Attorney, Agent, or Firm—Mary E. Gormley

[57] ABSTRACT

The present invention is concerned with a pseudorabies virus (PRV) vaccine comprising a polypeptide of the PRV glycoprotein gII or a fragment thereof which was shown to be the site of interaction of PRV neutralizing antibodies. Vector vaccines capable to express a polynucleotide fragment coding for such a polypeptide also form part of the present invention.

6 Claims, 7 Drawing Sheets

COMPARISON OF DNA SEQUENCE OF PHYLAXIA (WT) AND MAR-MUTANTS

```
Sequence        652              660              677
position         |                |                |
                 |                |                |
mIN-4     CATCTCGTGCGACC...CTGCACCGGCAAC...CTACGAGGACTACAA
                  Cys              |                |
                   |               |                |
m1/5      CATCTCGCGCGACC...CTGCACCCGCAAC...CTACGAGGACTACAA
                   |              Arg               |
                   |               |                |
m5/14     CATCTCGCGCGACC...CTGCACCGGCAAC...CTACGAGTACTACAA
                   |               |               Tyr
                   |               |                |
wt        CATCTCGCGCGACC...CTGCACCGGCAAC...CTACGAGGACTACAA
                  Arg             Gly              Asp
```

```
2020         2030         2040         2050         2060         2070         2080         2090
GCCGAGGAGATGATCCGGACGAGACGGCGACGGCGACGGCTCCTTCCGCTTCACGTCGCGGGCCCTGGGCGCTCCTTCGTCAGC
AlaGluGluMetIleArgAspGluThrArgAspGlySerPheThrSerArgAlaLeuGlyAlaSerPheValSer
                                                390                                             400
      2100         2110         2120         2130         2140         2150         2160         2170
GACGTCACGCAGCTGGACCTGCAGCCGGTGCACCTGGGCACTGCGTCCTCCGGACTGTGATCGACGGCCTGGAGGCCATCGACGCCATC
AspValThrGlnLeuAspLeuGlnArgValHisLeuGlyAspCysValLeuAlaSerGluArgGlyAlaIleAspAlaIle
                                                410                                             420
      2180         2190         2200         2210         2220         2230         2240         2250
TACCGGCGGCTACACAACACGCACGTGTGGCCGGACAAGGCCGGAGGTGTACCTGCCCCGGGGGCTTCGTGGTG
TyrArgArgArgTyrAsnAsnThrHisValLeuAlaGlyAspArgProGluValTyrLeuAlaArgGlyGlyPheValVal
                                                440                                             460
                                          450
      2260         2270         2280         2290         2300         2310         2320         2330
GCCTTCCGCCGCTGATCTCGAACGAGCTGGGCCAGCTGTACGCGCGCAGCTCGAGCGCTCGAGCGCCTCGCGGCGGTCGTG
AlaPheArgProLeuIleSerAsnGluLeuAlaGlnLeuTyrAlaArgGluLeuGluArgLeuGlyLeuAlaGlyValVal
                                                470                                             480
      2340         2350         2360         2370         2380         2390         2400         2410         2420
GGCCCCGCGGCCCGCGCCCGCTCCCCCGGGCTCCCCCCGGGCCCGGGACGCCGAGCGCCGGCGTCAAC
GlyProAlaAlaProAlaAlaAlaArgArgAlaArgSerProGlyProAlaGlyThrProGluProProAlaValAsn
                                                490                                             500
      2430         2440         2450         2460         2470         2480         2490         2500
GGCACGGGCACCTGCGCATCGCCACCACGGGCTCGGCGGAGTTTGCGCGCCTGCAGTTCACGGCGCTACGACCACATCCAGGCGCAC
GlyThrGlyHisLeuArgIleThrThrGlySerAlaGluPheAlaArgLeuGlnPheThrTyrAspHisIleGlnAlaHis
                                                520                                             540
                                          530
      2510         2520         2530         2540         2550         2560         2570         2580
GTGAACGACATGCTGGGCCATGCTGGGCCCGCATCGGCCGCAGAACAAGGACGTCGAGCTGAGCTGTCGGAGCGAGATGTCG
ValAsnAspMetLeuGlyArgIleAlaAlaThrAlaAlaArgCysGluLeuGlnAsnLysAspArgThrLeuTrpSerGluMetSer
                                                550                                             570
      2590         2600         2610         2620         2630         2640         2650         2660
CGCCTGAACCCCAGGCGCCGTGGGCCACGGCCCGGCCAGCCGCAGCCCAGCGCGCATGCTCGGCGACGTGATGGCCATC
ArgLeuAsnProSerAlaValAlaThrAlaAlaArgMetLeuGlyValSerAlaArgMetLeuGlyAspValMetAlaIle
                                                580                                             590
      2670         2680         2690         2700         2710         2720         2730         2740
TCGGGGTGCGTGGAGGTGCGCGGCGGCGTATACGTGCAGAACTCCATGCGTGCCCGGCGGAGCGGCACGTGCTACAGC
SerArgCysValGluValArgGlyGlyValTyrValGlnAsnSerMetArgValProGlyGluArgGlyThrCysTyrSer
                                                600                                             620
      2750         2760         2770         2780         2790         2800         2810         2820
CGCCCGCTGGTCACCTTCGAGCACAACGGCACACAGCACTTCGAGGGCGTGATCGAGGGCGACAACGAGCTCCTCATCTCG
ArgProLeuValThrPheGluHisAsnGlyThrGlyValIleGluGlyIleGlyAspAsnGluLeuLeuIleSer
                                                630                                             650
      2830         2840         2850         2860         2870         2880         2890         2900
CGCGACCTCATCGAGCCCTGCACCGGCAACCACCGGCGCTACTTTAAGCTGGGGAGCGGGTACGTGTACTACGAGGACTAC
ArgAspLeuIleGluProCysThrGlyAsnHisArgArgTyrPheLysLeuGlySerGlyTyrValTyrTyrGluAspTyr
                                                660                                             670
```

FIG. 1-3

```
2910       2920       2930       2940       2950       2960       2970       2980
AACTACGTGCGCATGGTGGAGGTGCCGAGACGATCAGCAGCGCGGGTGACCCTGAACCTGACGCTGCTGGAGGACGCGAG
AsnTyrValArgMetValGluValProGluThrIleSerThrArgValThrLeuAsnLeuThrLeuLeuGluAspArgGlu
                                     690                               700
2990       3000       3010       3020       3030       3040       3050       3060
TTCCTGCCCCTCGAGGTGTACACGCGGAGAGCTCGCAGACACGGGCCTTCTGGACTACAGACGGAGATCCAGCGCCGCAAC
PheLeuProLeuGluValTyrThrArgGluAlaArgHisThrGlyLeuLeuAspThrArgGluIleGlnArgArgAsn
        710                              720                              730
3070       3080       3090       3100       3110       3120       3130       3140    3150
CAGCTGCACGCGCTCAAGTTCTACGACATCGACCGCGTGGTCAAGGTGGACCACAACGTGGTGCTGCTGCGCGGCATCGCC
GlnLeuHisAlaLeuLysPheTyrAspIleAspArgValValLysValAspHisAsnValValLeuLeuArgGlyIleAla
                   740                             750
3160       3170       3180       3190       3200       3210       3220       3230
AACTTTTTCCAGGGCCTCGGCGACGTGGGCGCCGTGGCGCCGTCGGCAAGGTGGTCCTGGGCCCACGGGGGCCGTGATCTCGGCC
AsnPhePheGlnGlyLeuGlyAspValGlyAlaValAlaValGlyLysValValLeuGlyAlaGlyAlaThrGlyValIleSerAla
760                             770                             780
3240       3250       3260       3270       3280       3290       3300       3310
GTCGGCGGCATGGTGTCCTTCTGTCAACCCCTTCGGGGCGCTCGCCATCGGGCTGCTGGTGCTGGTGGCCGGCCTGGTCGCG
ValGlyGlyMetValSerPheLeuSerProPheGlyAlaLeuAlaIleGlyLeuLeuValLeuValAlaGlyLeuValAla
                 790                              800                              810
3320       3330       3340       3350       3360       3370       3380       3390
GCCTTCCTGGCCTACCGGCACATCTCGGCGCTGCTGCTGCAACCCCATGAAGGCCCTGTACCCGTACGACGAAGACGCTC
AlaPheLeuAlaTyrArgHisIleSerArgLeuLeuArgArgAsnProMetLysAlaLeuTyrProValThrThrLysThrLeu
                 820                              830                                840
3400       3410       3420       3430       3440       3450       3460       3470
AAGGAGGACGGCGTCGACAGGAGGCGTGGACGAGGCCAAGGTGGACCAGGCCCTGGACGACATGATCGGGACATGATCCATC
LysGluAspGlyValAspArgArgGlyValAspGluAlaLysLeuAspAspGlnAlaLeuAspAspMetIleArgTyrMetSerIle
                    850                              860
3480       3490       3500       3510       3520       3530       3540       3550
GTGTCGGCCCTCGAGCAGCAGGACACAAGGCGGCAAGAAGAACAGCGGGCCCGCGCTGGCCAGCCGGCCGTCGGGGGCG
ValSerAlaLeuGluGlnGlnGlnHisLeuLysAlaArgGlyLysAsnSerGlyProAlaLeuLeuAlaSerArgValGlyAla
      870                              880                              890
3560       3570       3580       3590       3600       3610       3620       3630
ATGGCCACGCGCCGCCACTACCAGCACGCCTCGAGAGCGAGGACGCCCGACGCCTGTAGCCCCCTCCCGGGGAAACAAT
MetAlaThrArgArgArgHisTyrGlnArgLeuGluSerGluAspProAspAlaLeu+++
        900                              910 913
3640       3650       3660       3670       3680       3690       3700       3710
AAAGATGCGCTTGTTTGGCAACACGTCGCGTCCGTCTCGCCCCTCTCCCCTCCGTCCCCTCTCCCTCCGTCCCCTCTCCC
3720       3730       3740       3750       3760       3770       3780       3790
CTCCGTCCCCTCTCCGTCCCCCTCTCCCCCTCCGTCCCCTCTCCCCTCCGTCCCCTCTCCCCTCCGTCCCCTCTCCCCTCCGT
3800       3810       3820       3830       3840       3850       3860       3870
CCCTCTCCCCTCCGTCCCCTCTCCCCTCCGTCCCCTCTCCCCTCCGTCCCCTCTCCCCTCCGTCCCCTCTCCCCTCCGTCCCCTCT
```

FIG. 1-4

```
3880       3890       3900       3910       3920       3930       3940       3950       3960
CCCCTCCGTCCCTCTCCCCTCCGTCCCTCTCCCCTCCGTCCCTCTCCCCTCCGTCCCTCTCCCCTC 3970       3980       3990       4000       4010       4020       4030       4040
           CGTCCCTCTCCCCCCCCGTCCCTCTCCGTCCCTCTCCCCCCCCGTCCCTCTCCCCTCTCCCTCCG 4050       4060       4070       4080       4090       4100       4110       4120
TCCCTCTCCGTCCCTCTCCCCTCCGTCCCTCTCCGTCCCTCTCCCCTCCGTCCCTCCGTCCCTC 4130       4140       4150       4160       4170       4180       4190       4200
           TCCCCCCCCGTCCCTCTCCCCCCGTCCCTCTCCCCGTCCCTCTCCCCTCCGTCCCTCTCCGTCCCTCTC 4210       4220       4230       4240       4250       4260       4270       4280
CCCTCCGTCCCTCTCCCCTCCCCGTCCCTCTCCCCTCCCCCCGTCCCTCTCCCCGTCCCTCTCCCT 4290       4300       4310       4320       4330       4340       4350       4360
           CCGTCCCTCTCCCCCCCCCCCGTCCCTCTCCCCCCCCCGTCCCTCTCCCCTCCGTCCCTCTCCCTCC 4370       4380       4390       4400       4410       4420       4430       4440
           GTCCCCTCCGTCCCTCTCCCCTCTCCCCTCCGTCCCTCTCCCCTCTCCCCTCCGTCCCTCTCCGTCCCT 4450       4460       4470       4480       4490       4500       4510       4520
           CTCCCCTCCGTCCCTCTCCCCTCTCCCCTCCGTCCCGACCACGATGACACGCACGC 4530       4540       4550       4560       4570       4580       4590       4600
           CGTGTGTACAGAATTAGAAAAAAACTTTATTTCCACACACGGGGGCAACGGGGGAAACCATACAACGGGGGGTCCGGGG 4610       4620       4630       4640       4650       4660       4670       4680
GCCGGTCACACGCGCCAGCTCTTGCGGGCGACGCGCGGGTGGCCGGTGAGGTCGATGACGGGTCGGGGGGTGCTGGTACAGGC 4690       4700       4710       4720       4730       4740       4750       4760       4770
           CGTCGTCCGCGGGTCCGCGGAGCCGCCTGGTCTGGTACACGTGGTCGGGCCCTGGGGCCCTGGGGACCGGCGGGGGTGGCGG 4780       4790       4800       4810       4820       4830       4840       4850
GGGCCGCGGAGTCGACCCCGCGGGGTCGCCTCGTGCGCGGCTCGTGCGCGGAGAGCCGGCGGCGCACGAAGCGCTGGG 4860       4870       4880       4890
           CGGCGGGAACGAGACCGCGGAAGCTGGTGCGCATGC
```

FIG. 1-5

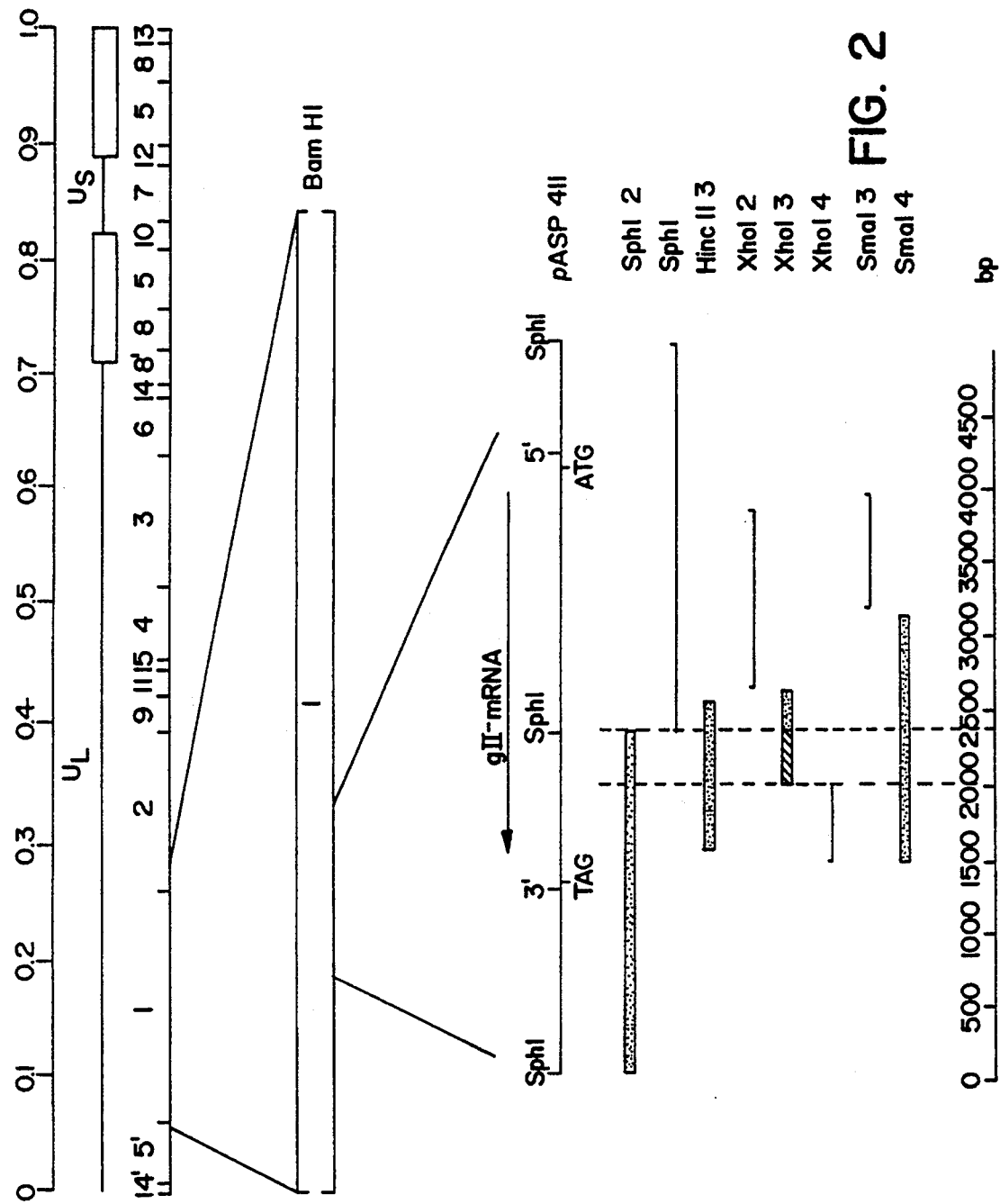

COMPARISON OF DNA SEQUENCE OF PHYLAXIA (WT) AND MAR-MUTANTS

| Sequence position | 652 | 660 | 677 |
|---|---|---|---|
| mIN-4 | CATCTCGTGCGACC... Cys | CTGCACCGGCAAC... | CTACGAGGACTACAA |
| m1/5 | CATCTCGGCGACC... | CTGCACCGGCAAC... Arg | CTACGAGGACTACAA |
| m5/14 | CATCTCGGCGACC... | CTGCACCGGCAAC... Gly | CTACGAGTACTACAA Tyr |
| wt | CATCTCGGCGACC... Arg | CTGCACCGGCAAC... | CTACGAGGACTACAA Asp |

FIG. 3

DNA ENCODING AMINO ACIDS 590-710 OF GLYCOPROTEIN GII OF PSEUDORABIES VIRUS

This is a continuation of U.S. Ser. No. 08/207,905, filed Mar. 7, 1994, now abandoned, which is a file wrapper continuation of U.S. Ser. No. 07/740,739, filed Aug. 6, 1991, now abandoned, which is a divisional of U.S. Ser. No. 07/383,833, filed Jul. 21, 1989, now U.S. Pat. No. 5,196,516, issued Mar. 23, 1993.

The present invention is concerned with a polypeptide having immunizing activity characteristic of the glycoprotein gII of pseudorabies virus (PRV), a polynucleotide coding for such a polypeptide, a recombinant DNA and a host comprising these, as well as a vaccine for the immunization of mammals against Aujeszky's disease.

Pseudorabies virus is the causative agent of Aujeszky's disease which induces serious economic losses especially among piglets in swine breeding farms and leads to latent infection in older animals.

PRV is a member of the herpes virus group, which contains in its core a double-stranded DNA molecule with a molecular weight of about $90 \times 10^6$ daltons (D), separated by inverted repeats into a long and a short unique region—$U_L$ and $U_S$, respectively. This DNA core is enclosed by an icosahedral capsid consisting of 162 capsomers. Around the capsid is found an amorphous structure called the tegument, which in turn is enclosed by the envelope with small spikes protruding from it. The envelope is acquired from the cellular membrane when the nucleocapsid buds through virus-modified patches of the cellular membrane. As a result the envelope largely consists of cellular membrane material with viral glycoproteins embedded therein. Probably these envelope glycoproteins are the only proteins exposed at the surface of intact PRV.

Five structural envelope glycoproteins of PRV whose genes are mapped and sequenced are indicated as gI, gII, gIII, gp 50 and gp 63, and have approximate molecular weights of 122, 155, 90, 50 and 63 kD, respectively (Lukàcs et al. (1985); J.Virol 53(1), 166–173; Hampl et al. (1984); J. Virol. 52 (2), 583–590). All these glycoproteins are sulphated as well, be it to varying degrees—gIII seems to be sulphated to a much higher extent than the others.

It is known that the herpes virus glycoproteins that are expressed at the surface are involved in the generation of virus neutralizing and protective antibodies. It has been shown that antibodies against gII can effectively neutralize PRV in vitro. Furthermore, after passive immunization of mice with antibodies against gII, protection against a lethal PRV infection is obtained. The glycoprotein gII is stably expressed by all PRV isolates tested so far, seems highly stable against mutation and it is believed that this protein is essential for virus replication.

It has been found, according to the present invention, that the glycoprotein gII can play an essential role in the neutralization of PRV by antibodies.

More in particular, it has been found that a specific region of gII is involved in said neutralization of PRV.

Therefore, the present invention is concerned with a polypeptide that, although it differs from the native glycoprotein gII, comprises at least one polypeptide fragment of gII, or a polypeptide having the same immunological characteristics as said polypeptide fragment.

The present invention is in particular concerned with a polypeptide fragment which for the gII glycoprotein of the PHYLAXIA strain is roughly positioned between the amino acid No's. 590 and 710 (FIG. 1). The corresponding fragments of the gII glycoproteins of other PRV strains form part of the present invention too.

Within the glycoprotein gII at least 4 epitopes are located which interact with distinct groups of monoclonal antibodies all capable to effectively neutralize the infectivity of PRV. These 4 groups of monoclonal antibodies are represented by the monoclonat antibodies produced by the hybridoma strains 1/5, IN4, N4 and N12, deposited with the European Collection of Animal Cell Cultures at Porton Down, U.K. under the deposit numbers 88080103, 88080102, 88080101 and 88080104, respectively. The hybridomas were all deposited on Aug. 1, 1988, at the Public Health Laboratory Service Centre for Applied Microbiology and Research, Porton Down, Salisbury, Wilts, U.K., SP4 OJG.

The polypeptide fragments corresponding with these epitopes also form part of the present invention.

The above-noted polypeptides according to the present invention are useful in or as synthetic vaccines for the immunization of mammals against Aujeszky's disease.

In some cases the ability to raise neutralizing antibodies of these polypeptides per se may be low. In these instances, for effective immunization, the immunogenicity of these polypeptides should be raised. This can be established, for example, by presenting the polypeptides coupled to some carrier. Suitable carriers for this purpose are macromolecules, such as natural polymers (proteins, like key-hole limpet hemocyanin, albumin, toxins), synthetic polymers like poly-amino acids (poly-lysine, poly-alanine), or micelles of amphiphilic compounds like saponins. Alternatively the polypeptides may be provided as polymers thereof, preferably linear polymers. These linear polymers may contain multiple copies of the same polypeptide, or of two or more different polypeptides according to the invention, and optionally may contain polypeptides representing fragments of other proteins (e.g. from PRV or from another pathogen) as well. The respective relevant polypeptides may be coupled directly to each other or may be coupled by means of a linking group, preferably one or more amino acid.

Both the polypeptide-carrier-bound and the linearly polymerized polypeptides according to the invention may advantageously be prepared as coupled products using recombinant DNA (rDNA) techniques whereby a polynucleotide coding for said polypeptide is inserted into a suitable expression vector.

A further alternative for the effective presentation of the polypeptides according to the invention is the covalent coupling of these polypeptides with amphiphilic compounds having adjuvant properties. Optionally these coupling products may be associated by non-covalent bonds to form complexes like micelles.

A further type of vaccine according to the invention comprises so-called vector vaccines. In this type of vaccine a polynucleotide sequence coding for a gII polypeptide according to the invention is grafted by recombinant techniques into the genetic material of a host microorganism (e.g. virus or bacterium) thereby enabling the latter to express the gII polypeptide within an in vitro cell system or directly in an animal to be protected against Aujeszky's disease. Suitable examples of vaccine vectors (without limiting the scope of the present invention) are for example pox viruses (such as vaccinia, cowpox, rabbit pox), herpes viruses (such as chicken pox (Varicella Zoster) virus), bacteriophages, adenoviruses, influenza viruses, or bacteria (such as *Escherichia coli* and Salmonella).

Still a further aspect of the present invention is a so-called anti-idiotype antibody to the gII polypeptide. Such an antibody is directed against the idiotype of the antibody specific for the gII polypeptide according to the invention. With the idiotype is meant that part of the antibody which is actually in direct contact with the polypeptide and which is responsible for the specific binding of that polypeptide to the antibody. Hence, the so-called variable fragment (Fv) of an anti-idiotype antibody exactly mimicks the epitope of the particular gII polypeptide. For this reason the anti-idiotype antibody for gII polypeptide or a variable fragment thereof, will upon administration to an animal give rise to antibodies against the particular gII epitope. An anti-idiotype vaccine for gII polypeptide may contain such an anti-idiotype antibody or an Fv part thereof, optionally bound to a carrier. Such an antibody may be a polyclonal antibody but more advantageously it may be a monoclonal anti-idiotype antibody or a mixture of several of these with different specificities.

The above-described vaccines are suitable for active immunization against Aujeszky's disease.

For passive immunization of animals against Aujeszky's disease use can be made of antibodies and more in particular monoclonal antibodies directed against the gII polypeptide of the invention or fragments thereof. Suitable representatives of such monoclonal antibodies against gII polypeptide are described in Example 1.

The antibodies and in particular monoclonal antibodies referred to in the description of the present invention can be prepared by methods known in the art such as immunization of an animal with gII polypeptide, immortalization of thus obtained antibody-producing cells and recombinant techniques.

Wherever throughout the present specification reference is made to recombinant techniques this refers to methods by which nucleic acids from different sources are linked to yield genetic material suited for replication and, where appropriate, for expression of the gII polypeptides according to the invention or antibodies against these.

In view of said recombinant techniques polynucleotides which code for a polypeptide according to the invention also form part of the present invention. More in particular this relates to polynucleotides coding for the entire gII polypeptide of about 121 amino acids as represented by the nucleotide base numbers about 2639 through about 3001 in FIG. 1. This also relates to subsequences thereof coding for a particular gII epitope, for chimeric polypeptides containing one or more of the gII epitopes or the entire about 121 amino acids gII polypeptide, and to polynucleotides which code for these same polypeptides making use of different codons for one or several of the respective constituting amino acids.

A vaccine according to the invention contains as its active ingredient either a gII-derived polypeptide, or an antibody against this polypeptide, or an anti-idiotype antibody for said polypeptide.

The vaccine with the gII-derived polypeptide or the anti-idiotype antibody therefore generally can be administered in a conventional active immunization scheme: single or repeated administration optionally preceded by or followed by an administration of inactivated PRV. The administration of the vaccine can be done e.g. intradermally, subcutaneously, intramuscularly or intravenously. Apart from the immunogenic compound the vaccine also may contain stabilizers, adjuvants, solubilizers, buffers, etc.

The vaccine may contain additionally other immunogens, like antigens of parvovirus, swine influenza virus, TGE virus, rotavirus, *Escherichia coli,* atrophic rhinitis, Erysipelas.

The vaccine with the antibodies against the gII-derived polypeptide may be administered as a single dose, optionally in a slow release dosage form, or repeatedly. The route of administration for this vaccine is preferably by intradermal, subcutaneous, intramuscular or intravenous injection. This vaccine may contain also stabilizers, solubilizers, buffers, etc.

DESCRIPTION OF THE DRAWINGS

FIGS. 1.1–1.5 are a representation of the DNA sequence and a portion of the corresponding amino acid sequence of the Phylaxia strain of Pseudorabies Virus.

FIG. 2 is a depiction of the wild-type resistant PRV phenotype.

FIG. 3 is a comparison of the DNA sequence of the wild-type and mar-mutant Phylaxia Strains.

EXAMPLES

PROCEDURES

1. Virus and cell culture

The virulent PRV strain PHYLAXIA was propagated and plaque-purified in Madin Darby bovine kidney cells (MDBK, ATCC CCL 221) or in SK-6 porcine kidney cells. The cells were maintained in Eagle minimal essential medium (MEM) with 10% newborn calf serum (Boehringer, Mannheim, FRG) and 100 units/ml penicillin and 100 μg/ml streptomycin. For growth of virus also BHK (baby hamster kidney) cells were used in Dulbecco modified minimal essential medium (DMEM). Virions were purified from the supernatant of infected cells (ca. 5 pfu/cell) by differential centrifugation and velocity sedimentation through 12 to 52% (w/v) sucrose gradient as recently described (Lukàcs et al., 1985). The virion band was aspirated, diluted with 0.2M Tris-HCl, 5 mM EDTA, 0.15M NaCl, and concentrated by pelleting in a SW27 rotor (Beckman) at 25.000 rpm, 4° C. for one hour.

2. Production of monoclonal antibodies

Monoclonal antibodies (Mab) against structural PRV proteins were produced as described (Lukàcs et al., 1985). In brief, the purified PRV virions were heat-inactivated at 60° C. for one hour and used for intraperitoneal immunization of BALB/c mice (50 μg protein in complete Freund adjuvant). After the last immunization the mouse spleen cells (ca. $3 \times 10^8$ cells) were fused with ca. $10^8$ Sp2/0-Ag14 myeloma cells by the use of polyethylenglycol (PEG). The cells were cultured on feeder cells (peritoneal mouse macrophages) in HAT medium containing 20% fetal calf serum (Boehringer, Mannheim, FRG) at 37° C. in a 5% $CO_2$ atmosphere. Hybridoma cell supernatant was tested for the production of PRV-specific antibodies in enzyme-linked immunoassay (ELISA). For that purpose, purified, sonicated PRV was coated onto 96 well plates (300 ng protein/well) and bound antibody was detected with peroxidase-labelled F(ab')$_2$ fragment of goat anti-mouse antibody (Tago Inc., Burlingame, USA). Positive hybridoma cultures were cloned and recloned by limiting dilution.

3. Determination of isotype

The immunoglobulin class of the individual Mab was determined by immunodiffusion. After ammonium-sulfate precipitation the hybridoma supernatants were tested with rabbit anti-mouse immunoglobulin sera (Nordic Immunol.) overnight at 4° C.

4. Radioimmuno precipitation

Infected cells (20 pfu/cell) were radiolabelled between 4 and 8 hours after infection (p.i.) either with [$^{35}$S]methionine (>1000 Ci/mM; Amersham Buchler, Braunschweig, FRG) or with D-[6-$^3$H]glucosanine (40 Ci/mM; Amersham Buchler, Braunschweig, FRG) as described (Lukàcs et al., 1985). Purified virions or infected cells were lysed in lysis buffer (phosphate-buffered saline containing 1% Nonidet P40, 0.1% deoxycholate, 0.1% sodium azide, 1 mM phenylmethylsulfonyl fluoride, 1 mM methionine and 2.5 mM potassium iodide). After centrifugation for 1 hour at 39.000 rpm in a Beckman 50 Tirotor, the lysates were preadsorbed with S. aureus and precipitated with hybridoma supernatants as described (Lukàcs et al., 1985). The washed immunoprecipitates were heated at 95° C. for 2 minutes in sample buffer (0.12M Tri-HCl pH 6.8, 4% SDS, 20% glycerol) in the presence or absence of 10% 2-mercaptoethanol and run in SDS-PAGE.

5. SDS polyacrylamide gel electrophoresis (SDS-PAGE)

The viral proteins were separated by SDS-PAGE in 7 or 10% polyacrylamide gels cross-linked with bisacrylamide as described earlier (Lukàcs et al., 1985).

6. Western blotting

Purified virion proteins were separated in SDS-PAGE, the gel renatured for 30 min. at room temperature in 50 mM NaCl, 10 mM Tris-HCl pH 7.0, 4M Urea and 0.1 mM dithiothreitol and transferred electrophoretically to nitrocellulose filter (Schleicher & Schüll, Dassel, FRG) in electrophoresis buffer without SDS for 2 hours at 30 V (1.0 A). After transfer the filter was incubated in PBS containing 3% bovine serum albumin (BSA) for 2 hours at room temperature and incubated overnight at room temperature with undiluted hybridoma supernatant. After washing the filter in PBS containing 0.1% Triton X-100 and in PBS with 1.0M NaCl, it was incubated with peroxidase-conjugated F(ab')$_2$ fragment of goat anti-mouse immunoglobulin G (Tago Inc., Burlingame, USA) and developed with chloronaphtol-H$_2$O$_2$ as described (Lukàcs et al., 1985).

7. Neutralization test

The in vitro neutralizing activity of the Mab was tested in the presence and in the absence of complement. Plaque-titrated virus was mixed together with ascites fluid of anti-gII Mab in a volume of 200 µl. As a source of complement 5% rabbit normal serum was used. The mixture was incubated at 37° C. for one hour followed by plaque titration on MDBK cells in 24 well plates (Costar). Serial dilutions of the reaction mixture (100 µl per well) were added to confluent monolayer cells and incubated for 1 hour at 37° C. After washing with PBS the cells were overlaid with semi-solid medium containing 1.5% methylcellulose. Plaques had developed after 3–4 days at 37° C. and the cells were fixed with 5% formalin before staining with crystal violet (1% in 50% ethanol).

8. Mice protection assays

Dilutions of Mab ascites fluid (1–3 mg IgG/ml) were made in MEM medium and 250 µl of them were injected intraperitoneally into C57/BL10 mice (6 weeks old). The animals were challenge infected 24 hours later with strain PHYLAXIA (22–27 TCID$_{50}$) and death was monitored during 10 to 14 days.

9. Grouping of anti-qII Mab

An indirect competition ELISA was performed for defining epitope specificity of anti-gII Mab. Hybridoma supernatant diluted with PBS containing 0.1% BSA was incubated overnight at 37° C. with clarified supernatant of PRV-infected cells.

Thereafter, 200 µl of this mixture was incubated in microtiter plates coated with Mab ascites fluid (0.2 µg protein per well) for one hour at 37° C. After three washing steps with 0.05% Tween 20 in PBS goat PRV hyperimmune serum (1:500 diluted) was added and incubated for another hour at 37° C., washed before incubating with peroxidase-conjugated rabbit anti-goat IgG (Dianova). After one hour at 37° C. and washing of the plate the reaction was developed with 1,2-phenylene-diamine (Sigma), stopped with 2M sulfuric acid and the optical density at 420 nm was determined.

10. Selection of "mar"-mutants

Natural occurring mutants resistent to the neutralization of individual anti-gII Mab (designated as mar-mutants) were selected by passaging strain PHYLAXIA in BHK cells in the presence of Mab and complement. For that purpose PRV and ascites fluid of Mab sufficient for complete neutralization of the wild-type virus (1–10% ascites) was incubated for 1–2 hours at 37° C. and thereafter plaque-titrated. Surviving virus plaques were picked, again neutralized with Mab and tested in neutralization assay. Single plaques were further propagated in the presence of Mab and complement (5% rabbit normal serum) and this procedure was repeated at least three times until stable neutralization-escape mutant virus had been obtained.

11. Surface immunoassay

Monolayer cell cultures were infected with strain PHYLAXIA or with the different mar-mutants and a plaque assay was performed as described in 7. omitting the fixation step. After removing the methylcellulose and washing the cells with medium, Mab diluted with normal horse serum was added.

All incubations were done at 37° C. unless otherwise indicated. After one hour the cells were washed and incubated with biotin-labelled anti-mouse IgG (Vectastain, ABC reagent) for another hour. Then the washed cells were incubated for 40 minutes with peroxidase-conjugated streptavidin-biotin complex (Vectastain, ABC reagent; diluted with PBS/0.1% BSA and preincubated for 30 minutes at room temperature), again washed and 4-chloro-1-naphtol/H$_2$O$_2$ used to detect the binding of Mab onto the surface of the infected cells (plaques).

12. DNA cloning

Purified PHYLAXIA DNA was cleaved with restriction endonucleases, and cloned into plasmids (pBR325, pUC19) according to standard procedures. Subcloning of vital DNA fragments in phage M13mp19 was achieved essentially as described (J. Messing, 1983, in: Methods Enzymol. Vol. 101, 20–78; ed. by R. Wu, L. Grossman & K. Moldave, Academic Press).

13. Marker rescue

Subconfluent BHK cells were co-transfected with total vital DNA (ca. 1.0 µg) and recombinant plasmid or double-stranded phage DNA (ca. 10 µg) according to the calcium phosphate precipitation method (Graham et al., 1973, Virology 52, 456–467). After the development of a cytopathogenic effect progeny virus was tested in in vitro neutralization and immunosurface assays.

14. DNA sequencing of the 'mar-epitopes'

The part of the gII-gene of the different mar-mutants predicted by marker rescue to contain the mutation, was sequenced and compared to wild-type PRV (strain PHYLAXIA) DNA-sequence. To this end, the purified DNA of the mutants m5/14, m1/5, mIN4, and mN4, respectively, was cleaved by restriction enzyme Sal I, the fragment 1A (METTENLEITER, T. C. ET AL., Virology 152, 66, 1986) was isolated from agarose gel and cloned into the bacterial plasmid pTZ19R (PHARMACIA). Three different cloned fragments 1A of each mutant DNA were used for double stranded DNA sequencing using T7-DNA polymerase (TABOR, S. & C. C. RICHARDSON, Proc. Natl. Acad. Sci. USA 84, 4767, 1987). To sequence both strands of each plasmid 20mer primers flanking the predicted 'mar-epitope' (gII sequence position 1750–1769 and 2126–2145, respectively) were synthesized. In addition, fragment 1A of PHYLAXIA was also sequenced by the same strategy.

15. Cloning of gII fragments and preparation of fusion proteins

Expression plasmid pTSX-4.

An 1180 bp XhoI fragment (isolated from plasmid pASP411, containing gII DNA sequences) was cloned in SmaI-cleaved pBDI. After induction of pTSX-4-containing bacteria a β-gal gII fragment fusion protein with an apparent mol.wt. of 77 kD is synthesized by this expression system.

Mass culture of pTSX-4 containing bacteria was grown in LB/Amp+0.5% glucose, IPTG-induction (0.5 mM), overnight at 37° C. Bacterial pellet was treated with lysozyme, NP40, DNAseI and ammonium sulphate precipitated. The lysate was separated in preparative SDS-PAGE and the fusion protein band cut out and electro-eluted with 1M $NH_4HCO_3$. Eluted material was lyophilized, suspended in PBS whereafter the concentration of fusion protein was determined according to Lowry (0.4 mg/ml) and tested for purity in SDS-PAGE/silver staining.

Expression plasmid pRZPS-3.

A 354 bp PstI fragment (isolated from plasmid pASP411, containing gII DNA sequences) was cloned in PstI-cleaved pUR291. After induction of pRZPS-3 containing bacteria a β-gal gII fragment fusion protein with an apparent mol.wt. of 125 kD is synthesized by this expression system. The preparation of said fusion protein was achieved as described above (concentration: 0.95 mg/ml).

EXAMPLE 1

Characterization of Mab 1.1. gII specificity

Hybridoma supernatants producing PRV-specific antibodies (as determined by ELISA) were further analyzed by radioimmuno-precipitation and Western blotting to select for gII-specific Mab. This major envelope constituent of PRV represents a glycoprotein complex consisting of three glycoproteins gIIa, gIIb, and gIIc linked together via disulfide bonds which are demonstrable under reducing conditions (in the presence of e.g. 2-mercapto-ethanol). Under non-reducing conditions a single protein with an apparent molecular weight of ca. 155 kd can be detected. After Western blotting the reaction of the Mab with the different gII subunits can be demonstrated.

1.2. Grouping of the anti-gII Mab

For the evaluation of different antigenic sites recognized by the Mab a competitive ELISA was used. After reacting with a first Mab the PRV was tested for its ability to bind to another second Mab coated onto the test-plate. The results indicated that at least 4 topologically distinct domains exist on the gII (Table 1).

TABLE 1

Competitive ELISA for grouping different anti-gII Mab

| Mab 1 | Mab 2 | | | | | | |
|---|---|---|---|---|---|---|---|
| | 5/14 | N4 | N3 | IN4 | 1/5 | 2/22 | N12 |
| 5/14 | + | + | + | − | − | − | − |
| N4 | + | + | + | − | − | − | − |
| N3 | + | + | + | − | − | − | − |
| IN4 | + | + | + | + | + | − | − |
| 1/5 | ± | + | ± | ± | + | − | − |
| 2/22 | | | | | | + | |
| N12 | − | − | − | ± | ± | ± | + |
| Group: | A | | | B | C | D | E |

Legend:
Mab1=coated onto plate
Mab2=used for preincubation with virus
+ refers to inhibition of binding after Mab 2 had reacted with PRV
− refers to no inhibition
± indicates no unequivocal conclusion as to inhibition in the ELISA
blanks mean that no ELISA was done for that case.

1.3. Neutralizing activity

The ability of the anti-gII Mab to neutralize PRV in vitro was tested both with and without complement. It could be shown that all Mab were reactive in the presence of complement, and one Mab neutralized PRV also in the absence of complement (Table 2). Fractionated PRV hyperimmune serum with a high titer of neutralizing antibodies showed that the gII-specific fractions did also neutralize PRV in vitro.

TABLE 2

Properties of anti-gII Mab

| Mab # | Isotype | Neutralization | | Protection | |
|---|---|---|---|---|---|
| | | +C′ | −C′ | % protec. | died/total |
| 5/14 | IgG 1 | 4.4 | − | 25 | 15/20 |
| IN4 | IgG 2b | 5.1 | − | 5 | 19/20 |
| N4 | IgG 2a | 5.3 | − | 37½ | 5/8 |
| N3 | IgG 2b | 5.0 | − | 27 | 13/18 |
| 1/5 | IgG 2b | 5.3 | − | 35 | 13/20 |
| 2/22 | IgG 1 | 2.0 | − | 50 | 5/10 |
| N12 | IgG 1 | 3.4 | 2.7 | 84 | 3/19 |

Legend:
Neutralization test was performed in the presence of complement (+C′; 5% rabbit normal serum) or in the absence of complement (−C′). Titers are given as $-\log^{10}$ of antibody dilution showing 50% plaque reduction.

1.4. Protective activity

Passive immunization of mice with different anti-gII Mab conferred different degrees of protection against a lethal challenge infection with strain PHYLAXIA. The protection rate ranged between 5 to 85% of animals surviving challenge (Table 2).

Using combinations of some anti-gII Mab a synergistic effect could be observed in protection. Whereas the application of the single Mab conferred only partial protection of mice (see Table 1), the combined immunization increased the protection rate up to 70 to 100% of animals (Table 3).

TABLE 3

Protection of mice after passive immunization with combined application of anti-gII Mab.

| Mab # | Group | Protection % | (protected/total) |
|---|---|---|---|
| 5/14 | A | 100 | (10/10) |
| IN4 | B | | |
| 2/22 | D | | |
| 5/14 | A | 70 | (7/10) |
| 1/5 | C | | |
| N3 | A | 80 | (8/10) |
| N4 | A | | |
| 1/5 | C | | |

From the data described above it appears that antibodies against gII might play an important role in neutralizing PRV infectivity. Furthermore, this envelope protein is found to be expressed regularly and in similar amounts in numerous PRV strains and field isolates tested. Finally, the gII of PRV displays extensive homology to the glycoprotein gB of herpes simplex virus (Robbins et al., 1987) which is involved in natural killer cell recognition and cell-mediated immunity.

EXAMPLE 2

Characterization of the mar-mutants

The following mutants could be obtained after selection with the Mab 5/14 (m5/14), Mab 1/5 (m1/5$_{(1)}$ and m1/5$_{(2)}$), Mab IN4 (mIN4$_{(1)}$ and mIN4$_{(2)}$), and Mab N4 (mN4$_{(1)}$ and mN4$_{(2)}$).

In addition to their resistance in neutralization, the mutants also did not bind the homologous Mab in immunosurface binding assay. The mutants m1/5 and mIN4 were completely neutralized and recognized by the heterologous Mab. The mutant m5/14 was resistant in neutralization against the Mab N3 and N4, but neutralized by the other heterologous Mab. Analogous results were found for the mutant mN4 and the Mab 5/14 and N3. After testing both mutants in immunosurface binding assay the m5/14 virus did not react with the Mab N4, but bound the other heterologous Mab. In contrast, the mN4 virus displayed also binding of the Mab 5/14 (Table 4).

TABLE 4

| mAB | Cross Neutralization Test "mar"-Mutants | | | |
|---|---|---|---|---|
| | m5/14 | m1/5 | mIN4 | mN4 |
| 5/14 | − | + | + | − |
| IN4 | + | + | − | + |
| N4 | − | + | + | − |
| N3 | − | + | + | − |
| 1/5 | + | − | + | + |
| A4 | + | + | + | + |
| A15 | + | + | + | + |
| A25 | + | + | + | + |
| A33 | + | + | + | + |
| B3 | + | + | + | + |
| B16 | + | + | + | + |
| B24 | + | + | + | + |

Legend: + neutralization
− no neutralization

These results indicate that 5/14 and N4 antibodies might be directed against two overlapping epitopes. Alternatively, the mutation in m5/14 might have led to a conformational alteration inhibiting binding of the Mab N4.

In conclusion, the existence of at least 4 different epitopic sites of neutralizing antibodies in gII was demonstrated, which is in accordance with the results of the competitive ELISA (1.2.). Domain A is recognized by the Mab 5/14, N4 and N3, domain B specific for Mab 1/5, C for Mab IN4 and at least one additional epitope recognized by the remaining neutralizing Mab.

The expression of gII in the mar-mutants was investigated by radioimmunoprecipitation tests. In principle, the same pattern of reactivity was found as already described for neutralization and immunosurface binding of the different anti-gII Mab. All mutants produced a gII protein qualitatively not altered as compared to wild-type PRV. It appears that the mutant mIN4 might synthesize reduced amounts of gII. No reaction was found after testing the mutant m5/14 and m1/5 with the Mab used for selection, whereas the homologous Mab precipitated only low amounts of gII of the two other mutants. The heterologous Mab precipitated gII of all mar-mutants, except of Mab 5/14 which was not able to precipitate the mutated gII from mN4 virus.

Thus, it can be concluded that the resistant phenotypes arose from mutations which either altered the conformation or the amino acid sequence of the epitopic sites of gII.

EXAMPLE 3

Identification of the 'mar-epitope'

This was done using so-called 'marker rescue' experiments. In this assay cloned wild-type DNA fragments spanning the complete gII coding region were used to replace the corresponding parts in the mutant virus genome. After co-transfection of mutant virus DNA and cloned DNA fragment the progeny virus was tested in neutralization and immunosurface binding assay. As depicted in FIG. 2 the wild-type phenotype was rescueable with all mar-mutants after co-transfection with the complete gII gene (pASP411), with the SphI fragment 2, HincII fragment 3, XhoI fragment 3, and Sma fragment 4. After co-transfection of the mar genomes with the other DNA fragments (and also with control plasmids pBR325 and M13mp19) the resistant phenotype was retained. These results demonstrate that the epitopic sites of the neutralizing antibodies used for selection of the mutants are located in a region of 356 basepairs in size. The upper limits of this gII region are defined by the SphI fragment 2 (5' end) and the XhoI fragment 3 (3' end). The DNA sequence of strain PHYLAXIA (FIG. 1) reveals that this part of gII is quite hydrophilic and is predicted as a domain with high antigenic index. Furthermore, this region ends ca. 40 amino acids upstream of the putative transmembrane domain of gII.

EXAMPLE 4

DNA sequence of the different 'mar-epitopes'

The DNA sequence of the mar-mutants m5/14, m1/5, and mIN-4 (both strands between position 1797 and 2103 were sequenced) was found to be altered in single bases differing from each other (FIG. 3), the mutant mN-4 exhibited the identical point mutation as m5/14. Sequencing of three different cloned fragments 1A of each mutant DNA showed identical results, thus the demonstrated single base exchanges do not represent cloning artefacts. The mutation affected always the first base of a codon leading to the amino acid exchange as depicted in FIG. 3.

Comparison of the predicted peptide structure of wt-gII and gII of the three mar-mutants revealed the loss of highly antigenic parts, which are exactly located around positions 652, 660 and 677, respectively. These alterations in the gII-genes of the mar-mutants explain the loss of binding of monoclonal antibodies resulting in the inability to neutralize the mutant virus.

EXAMPLE 5

Antibody response of gII fragment fusion proteins

The fusion proteins expressed by pRZPS-3 and pTSX-4 were purified by β-Galactosidase affinity chromatography according to the instructions of the manufacturer (Pharmacia).

The purified fusion proteins were emulsified in mineral oil using Tween 80 and Span 80 as emulsifiers.

With each fusion protein two rabbits were injected at different sides and boostered twice at 6-weeks interval. The sera obtained were tested in the Elisa and in the virus neutralisation (VN) test. After one injection antibodies reacting in the Elisa were found for both fusion proteins. However, after two booster injections neutralising antibodies were only found for the fusion protein resulting from pRZPS-3 (Table 5, rabbit no. 3869 and 3870).

TABLE 5

Antibody response of fusion proteins

| Rabbit No. | fusion protein | Antibody titer | | | |
|---|---|---|---|---|---|
| | | Elisa | | VN | |
| | | 0 | 6 weeks | 0 | 22 weeks |
| 3869 | pRZPS-3 | — | 2 | — | 2 |
| 3870 | pRZPS-3 | — | 8 | — | 8 |
| 3871 | pTSX-4 | — | 128 | — | — |
| 3872 | pTSX-4 | — | 64 | — | — |

These results demonstrate that neutralizing sites are located in a gII fragment encoded by a 354 bp PstI fragment of the gII gene.

We claim:

1. A DNA molecule that codes for a polypeptide having an immunizing activity characteristic of glycoprotein gII of Pseudorabies virus, comprising a fragment of glycoprotein gII of Pseudorabies virus containing the amino acid sequence 590–710 of said gII, or subsequences thereof containing at least one epitope that reacts with Pseudorabies virus neutralizing antibodies, wherein the DNA molecule is substantially free of DNA sequences that code for portions of the gII protein outside of the region coding for amino acids 590–710.

2. A DNA molecule according to claim 1 made by recombinant techniques.

3. A host microorganism containing a DNA molecule according to claim 1.

4. A DNA molecule according to claim 1, comprising the DNA sequence positioned between about nucleotide 2639 and 3001 depicted in FIG. 1 or subsequences thereof that code for subsequences of the amino acid sequence 590–710 which contain at least one epitope that reacts with Pseudorabies virus neutralizing antibodies.

5. A DNA molecule according to claim 1, wherein the polypeptide is recognized by a monoclonal antibody selected from the group consisting of 1/5, IN4 and N4.

6. A DNA molecule according to claim 1, which is coupled to a nucleic acid sequence encoding an immunogenic carrier.

* * * * *